(12) United States Patent
Corl (10) Patent No.: US 12,167,931 B2
(45) Date of Patent: Dec. 17, 2024

(54) SENSOR INTERFACE DEVICE PROVIDING DIGITAL PROCESSING OF INTRAVASCULAR FLOW AND PRESSURE DATA

(71) Applicant: VOLCANO CORPORATION, San Diego, CA (US)

(72) Inventor: Paul Douglas Corl, Palo Alto, CA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 1292 days.

(21) Appl. No.: 16/428,716

(22) Filed: May 31, 2019

(65) Prior Publication Data

US 2019/0307416 A1 Oct. 10, 2019

Related U.S. Application Data

(62) Division of application No. 14/850,656, filed on Sep. 10, 2015, now abandoned.
(Continued)

(51) Int. Cl.
*A61B 8/00* (2006.01)
*A61B 5/00* (2006.01)
(Continued)

(52) U.S. Cl.
CPC .............. *A61B 8/06* (2013.01); *A61B 5/6851* (2013.01); *A61B 8/0891* (2013.01); *A61B 8/12* (2013.01);
(Continued)

(58) Field of Classification Search
CPC ........... A61B 8/06; A61B 8/12; A61B 8/4483; A61B 8/461; A61B 8/5223; A61B 5/6851; A61B 8/0891; A61B 8/488; A61B 5/6852
See application file for complete search history.

(56) References Cited

U.S. PATENT DOCUMENTS 5,623,930 A * 4/1997 Wright ................ A61B 8/06
600/456
6,666,824 B2 * 12/2003 Rust .................... A61B 8/00
600/443
(Continued)

FOREIGN PATENT DOCUMENTS

JP 11299776 A 11/1999
WO 2011062683 A1 5/2011

OTHER PUBLICATIONS

"Multiplexing", Feb. 16, 2006m Retrieved from the internet: URL:https://www.staff.ncl.ac.uk/r.carrasco/Multiplexing/ppt.

*Primary Examiner* — Joel Lamprecht
*Assistant Examiner* — James F McDonald, III (57) ABSTRACT

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries by monitoring fluid flow. In some embodiments, the devices, systems, and methods of the present disclosure receive analog sensor data that includes fluid flow data and digitizes the analog sensor data according to a quadrature sampling rate. A weighted accumulator performs a baseband conversion on the digitized sensor data and may perform other signal processing steps. The processed data is then provided for use in any one of a number of diagnostic assessments.

18 Claims, 4 Drawing Sheets

Related U.S. Application Data (60) Provisional application No. 62/049,205, filed on Sep. 11, 2014.

(51) Int. Cl.
*A61B 8/06* (2006.01)
*A61B 8/08* (2006.01)
*A61B 8/12* (2006.01)

(52) U.S. Cl.
CPC ............ *A61B 8/4483* (2013.01); *A61B 8/461* (2013.01); *A61B 8/488* (2013.01); *A61B 8/5223* (2013.01); *A61B 5/6852* (2013.01)

(56) References Cited

U.S. PATENT DOCUMENTS

| | | | | |
|---|---|---|---|---|
| 8,600,299 | B2* | 12/2013 | Randall | A61B 8/4483 455/39 |
| 2002/0123685 | A1* | 9/2002 | Miwa | G01S 7/52046 600/443 |
| 2003/0187354 | A1* | 10/2003 | Rust | A61B 8/00 600/437 |
| 2003/0236443 | A1* | 12/2003 | Cespedes | A61B 5/02007 600/29 |
| 2005/0148903 | A1* | 7/2005 | Diamantopoulos | A61B 5/6859 600/587 |
| 2005/0251041 | A1* | 11/2005 | Moehring | A61B 8/488 600/455 |
| 2006/0241478 | A1 | 10/2006 | Lewis | |
| 2007/0010805 | A1 | 1/2007 | Fedewa | |
| 2008/0110261 | A1* | 5/2008 | Randall | G01S 7/52023 73/64.41 |
| 2008/0114255 | A1 | 5/2008 | Schwartz | |
| 2008/0156106 | A1* | 7/2008 | Zhang | G01F 1/663 600/453 |
| 2008/0269572 | A1* | 10/2008 | Kanz | A61B 5/0006 600/301 |
| 2010/0305449 | A1 | 12/2010 | Wegener | |
| 2012/0010508 | A1* | 1/2012 | Sokulin | A61B 8/461 600/443 |
| 2012/0101355 | A1* | 4/2012 | Gopinathan | A61B 5/1075 600/547 |
| 2013/0015975 | A1* | 1/2013 | Huennekens | A61B 5/0084 340/573.1 |
| 2013/0303888 | A1 | 11/2013 | Deladi | |
| 2014/0056099 | A1 | 2/2014 | Hancock | |
| 2014/0276143 | A1 | 9/2014 | Corl | |
| 2015/0289749 | A1 | 10/2015 | Stigall | |

\* cited by examiner

SENSOR INTERFACE DEVICE PROVIDING DIGITAL PROCESSING OF INTRAVASCULAR FLOW AND PRESSURE DATA

CROSS REFERENCE TO RELATED APPLICATIONS

The present application is a divisional application of U.S. patent application Ser. No. 14/850,656, filed Sep. 10, 2015, which claims priority to and the benefit of U.S. Provisional Patent Application No. 62/049,205, filed Sep. 11, 2014, each of which is hereby incorporated by reference in its entirety.

TECHNICAL FIELD

The present disclosure relates generally to the assessment of vessels and, in particular, to systems and techniques for the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

Technology innovations and trends in the healthcare industry are driving increased adoption of intravascular diagnostic procedures in interventional cardiology practice. The use of intravascular diagnostic tools to complement the traditional external diagnostic procedures (e.g., angiography) has been shown to promote more appropriate and effective application of interventional procedures, leading to improved patient satisfaction and increased cost-effectiveness. In particular, diagnostic equipment and methods have been developed for assessing vascular obstructions and other vascular disease using miniature sensors placed at the distal end of a flexible elongate member such as an intravascular catheter or guide wire used for catheterization procedures. For example, known intravascular medical sensing techniques include intravascular pressure measurement for calculation of fractional flow reserve (FFR) or instantaneous wave-free ratio (iFR), Doppler ultrasound blood flow measurement for determination of coronary flow reserve (CFR) or other flow-related parameters, intravascular ultrasound (IVUS) imaging, and optical coherence tomography (OCT) imaging. Each of these techniques may be suited for different diagnostic situations.

To facilitate improved diagnosis to guide more appropriate treatment, healthcare facilities typically maintain a multitude of intravascular diagnostic, and sensing modalities for use during an interventional procedure in the catheter lab. Recently, processing systems have been developed that collect medical data from a plurality of different imaging, treatment, diagnostic, and sensing tools and process the multi-modality medical data. Such multi-modality systems are valued for reducing the clutter in the cath lab by reducing the number of separate systems that are needed to support the multitude of technologies, and for the synergies that arise from combining information from different sensing technologies into a single unit. In these multi-modality systems, efficient and flexible signal processing systems are valued for facilitating a more compact system with greater capabilities and adaptability.

While existing diagnostic systems have proved useful, they are not without drawbacks. Many legacy systems rely on highly specialized analog circuitry to process sensor data. Compared to traditional analog approaches, modern digital signal processing systems may provide increased flexibility and adaptability, reduced power consumption, more compact packaging, enhanced stability, and improved performance.

Accordingly, there remains a need for improved devices, systems, and methods for obtaining diagnostic information, such as vascular data used to assess the severity of a blockage in a vessel and, in particular, a stenosis in a blood vessel. Improved diagnostic systems that perform signal processing in the digital domain have the potential to bring improved performance to existing diagnostic and therapeutic practices and to pave the way for further advances.

SUMMARY

Embodiments of the present disclosure are configured to assess the severity of a blockage in a vessel and, in some examples, a stenosis in a blood vessel utilizing an intravascular device having one or more sensing devices measuring flow, pressure, and/or temperature.

In some instances, a diagnostic system is provided that receives sensor information from the sensors of the intravascular device. The diagnostic system includes a patient interface module that is operable to process analog flow sensor data received from the intravascular device. The patient interface module includes an analog-to-digital converter operable to sample the analog flow sensor data according to a quadrature sampling rate to produce digital flow sensor data. The patient interface module also includes a signal processing resource operable to perform a baseband conversion on the digital flow sensor data to produce baseband flow sensor data. The patient interface module also includes an interface subunit operable to output the baseband flow sensor data. The analog flow sensor data may include a measurement of fluid flow velocity within a vessel. In such embodiments, the quadrature sampling rate may correspond to a center frequency of the ultrasound transducer. For example, in one such embodiment, the quadrature sampling rate is approximately equal to four times the center frequency. This quadrature sampling method simplifies many of the steps and calculations involved in the baseband conversion of the digital sensor data and may make digital baseband conversion an attractive alternative to analog baseband conversion.

In some instances, a method of assessing a vessel of a patient is provided that includes: receiving analog sensor data including a measurement of fluid flow; digitizing the analog sensor data to obtain digital sensor data using a quadrature sampling rate corresponding to a center frequency of an ultrasound transducer used in obtaining the analog sensor data; performing a baseband conversion of the digital sensor data using a computing system to obtain digital baseband sensor data; and outputting a representation of a measurement of fluid flow based on the digital baseband sensor data to a display for use in a diagnostic assessment. In some embodiments, the quadrature sampling rate is defined by the equation:

$$\text{quadrature sampling rate} = 4/(2N+1) \times \text{the center frequency}$$

where N is an integer greater than or equal to zero. For example, in one such embodiment, the quadrature sampling rate is substantially equal to four times the center frequency of the ultrasound transducer. In some instances, the baseband conversion may include mixing the digitized samples with in-phase and quadrature reference signals to produce in-phase and quadrature components, and then performing interpolation and low-pass filtering on the in-phase component and on the quadrature component.

Other devices, systems, and methods specifically configured to interface with such devices and/or implement such methods are also provided. Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1:
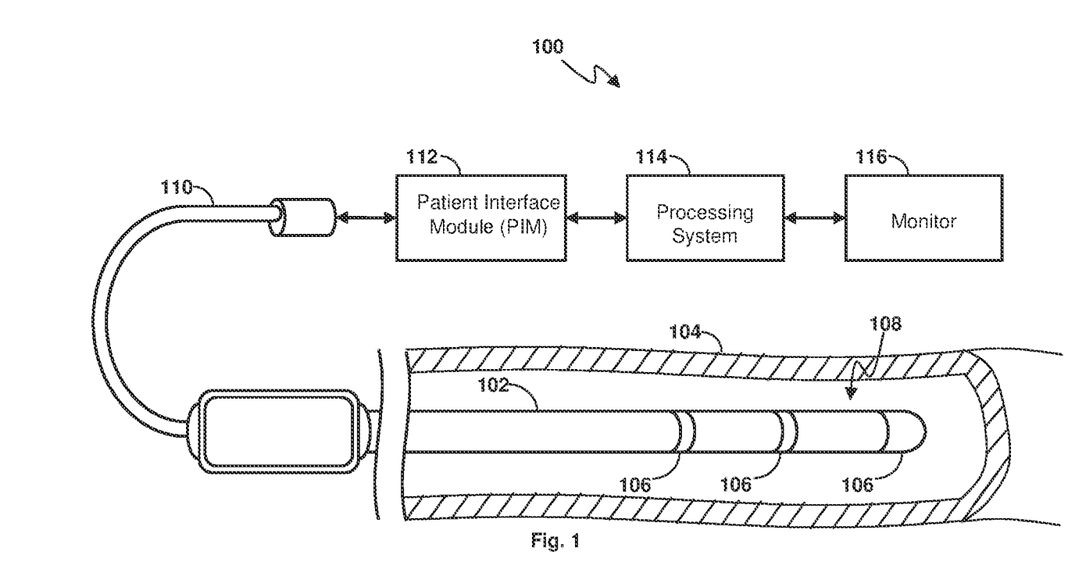
FIG. 1 is a diagrammatic schematic view of a medical diagnostic system showing a distal portion of an associated intravascular device according to an embodiment of the present disclosure.

Referring to FIG. 1, shown therein is a diagnostic system 100 according to an embodiment of the present disclosure. In general, the diagnostic system 100 may be a single modality medical system or a multi-modality medical system. In that regard, a multi-modality medical system provides for coherent integration and consolidation of multiple forms of acquisition and processing elements designed to be sensitive to a variety of methods used to acquire and interpret physiological and morphological information and/or coordinate treatment of various conditions in the human vasculature.

As shown, the diagnostic system 100 includes a sensing instrument 102. The sensing instrument 102 may be any form of device, instrument, or probe sized and shaped to be positioned within a vessel. In the illustrated embodiment, the instrument 102 is generally representative of a guide wire. In other embodiments, the instrument 102 may be a catheter, including a rapid-exchange catheter or an over-the-wire catheter. Generally, the instrument 102 is sized such that it can be positioned within a vessel without significantly impairing fluid flow through the vessel. Accordingly, in some instances the instrument 102 has an outer diameter of 0.035", 0.018", 0.014" or less.

As shown in FIG. 1, the distal end of the instrument 102 is advanced into a vessel 104. Vessel 104 represents fluid filled structures, both natural and man-made, within a living body and can include for example, but without limitation, structures such as: blood vessels (arteries and veins), portions of the heart, heart valves, stents, shunts, filters and other natural or artificial devices positioned within the body.

The instrument 102 is configured to obtain diagnostic information about fluid flow within the vessel 104 (or about the vessel 104 itself) in which the instrument 102 is positioned. In that regard, the instrument 102 includes one or more sensing elements, transducers, and/or other monitoring elements (referred to generally as sensors 106) positioned within a distal portion of the instrument 102. For example, one or more sensors may be disposed at the distal tip 108 of the instrument. The sensor(s) 106 are configured to obtain the diagnostic information such as one or more of flow velocity, volumetric flow, intravascular pressure, temperature, images (including images obtained using intravascular ultrasound, optical coherence tomography, thermal, and/or other imaging techniques), and/or combinations thereof.

In the illustrated embodiment, the instrument 102 includes at least one sensor 106 configured to monitor fluid flow within a vessel. Some exemplary flow monitoring sensors 106 incorporate one or more ultrasound transducers. For example in some instances, the flow monitoring sensor 106 is an ultrasound transducer configured to detect Doppler-shifted ultrasound echo signals indicative of blood flow velocity.

Additionally or in the alternative, the instrument 102 may include at least one pressure monitoring sensor 106. Exemplary pressure monitoring sensors 106 include a piezoresistive pressure sensor, a piezoelectric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using microelectromechanical systems (MEMS) technology and/or other suitable manufacturing techniques. An example of a commercially available guide wire product that includes both flow velocity and pressure measuring elements is the ComboWire® XT pressure and flow guide wire available from Volcano Corporation.

When the sensors 106 are active, a communications channel 110, such as an optical fiber, a conductor bundle, and/or a wireless transceiver, present in the instrument 102 carries sensor data to a patient interface module (PIM) 112 coupled to the proximal end of the instrument 102. The PIM 112 is operable to receive medical sensor data collected by the instrument 102 and the corresponding sensors 106, and is operable to transmit the received data to the processing system 114. In various embodiments, the PIM 112 transmits the medical sensor data over a USB connection, but in other embodiments an Ethernet connection, a Thunderbolt® connection, a FireWire connection, or some other high-speed data bus connection can be utilized. In other instances, the PIM 112 may be connected to the processing system 114 via wireless connections using IEEE 802.11 Wi-Fi standards, Ultra Wide-Band (UWB) standards, wireless FireWire, wireless USB, or another high-speed wireless networking standard.

In addition to transmitting data between the instrument 102 and the processing system 114, the PIM 112 may perform processing of the sensor data prior to transmitting the data. In examples of such embodiments, the PIM 112 performs amplification, filtering, time-stamping, identification, and/or aggregating of the data. The PIM 112 may also transfer data from the processing system 114 to the sensors 106 of the instrument 102. In an exemplary embodiment, this feedback data include commands to enable and disable sensors and/or to configure modes of operation for individual sensors. In some embodiments, the PIM 112 also supplies power to drive the operation of the sensors 106.

The processing system 114 to which the PIM 112 is coupled governs sensor operation and data acquisition, processing, interpretation, and display. In that regard, the processing system 114 receives sensor data from the sensors 106 of the instrument 102 via the PIM 112, processes the sensor data to render it suitable for display, and presents the processed sensor data on a user display or monitor 116.

In various embodiments, the diagnostic system 100 includes a computing system comprising any combination of hardware and software in order to acquire, process, and display medical data. In embodiments in which the diagnostic system 100 includes a computer workstation, the system includes a processor such as a microcontroller or a dedicated central processing unit (CPU), a non-transitory computer-readable storage medium such as a hard drive, random access memory (RAM), read-only memory (e.g., CD-ROM, DVD, etc.), a video controller such as a graphics processing unit (GPU), and/or a network communication device such as an Ethernet controller and/or wireless communication controller. The hardware of the diagnostic system 100 may be programmed to execute steps associated with the data acquisition and analysis described herein. Accordingly, it is understood that any steps related to data acquisition, data processing, instrument control, and/or other processing or control aspects of the present disclosure may be implemented by the diagnostic system 100 using corresponding instructions stored on or in a non-transitory computer readable medium accessible by the processing system. Further, it is understood that the different processing and/or control aspects of the present disclosure may be implemented separately or within predefined groupings using a plurality of computing devices. The present disclosure encompasses any divisions and/or combinations of the processing and/or control aspects described below across multiple computing devices.

Figure 2:
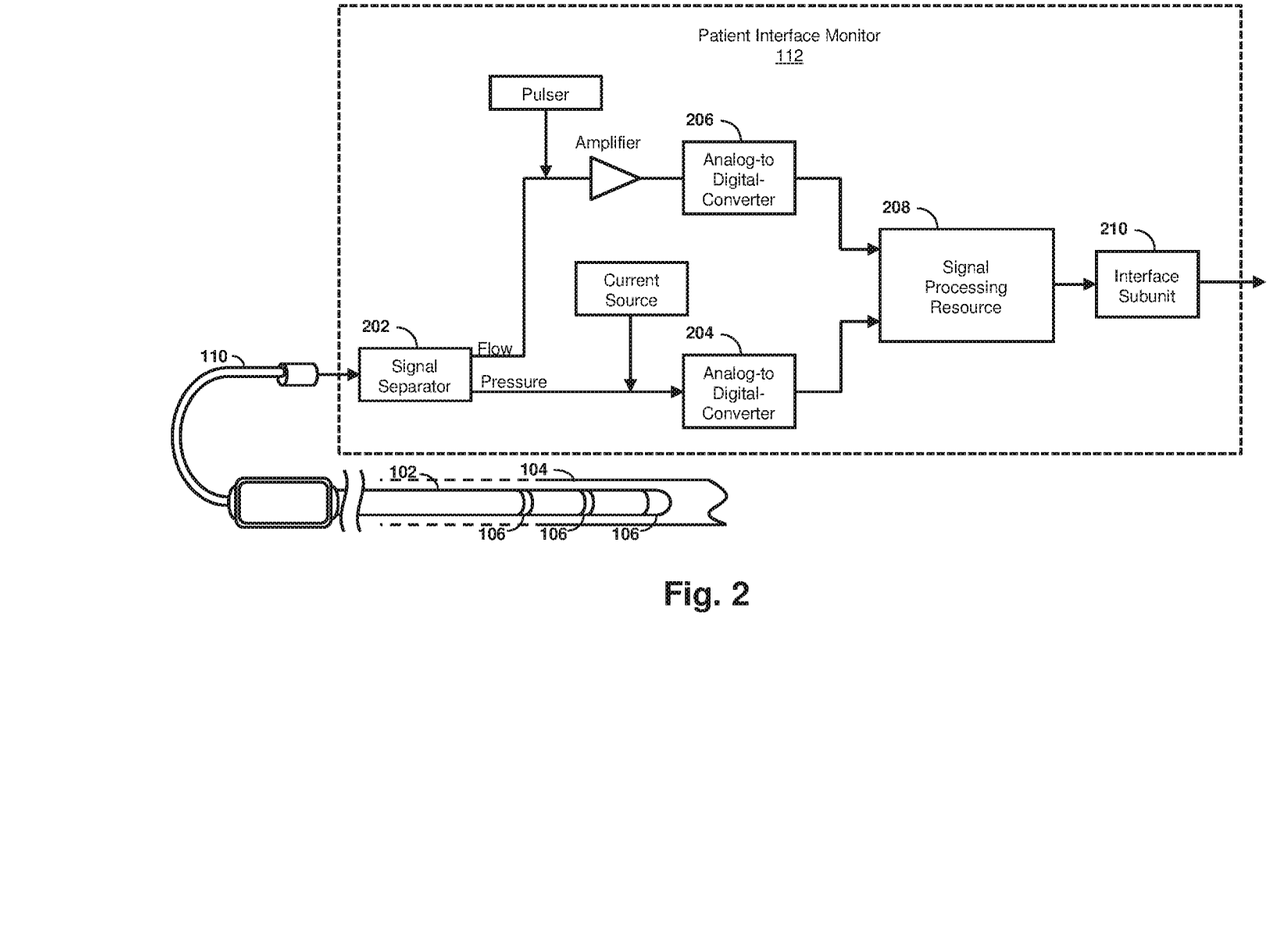
FIG. 2 is a diagrammatic schematic view of a patient interface module (PIM) of a diagnostic system according to an embodiment of the present disclosure.

Referring next to FIG. 2, an exemplary PIM 112 is shown in more detail according to an embodiment of the present disclosure. The PIM 112 offers an improved instrument interface that utilizes high-sampling-rate analog-to-digital conversion to enable much of the signal processing to be performed in the digital domain, rather than making more extensive use of analog signal processing electronics. For example, in some embodiments, analog components are used to perform data processing steps including baseband conversion, interpolation and low-pass filtering, integrate-and-hold, and/or clutter filtering to remove low frequency and stationary echoes. These components operate on an analog representation of the sensor data (voltage waveforms). Historically, analog signal processing has provided a relatively compact and efficient method for handling high frequency signals, but with limited flexibility for adopting to varying signal processing tasks, while it was digital electronics was limited in its ability to convert and process high frequency analog signals. However, modern digital electronics can now accommodate high frequency analog-to-digital conversion and signal processing tasks in an even more compact and power-efficient format compared to traditional analog electronics, while providing greatly enhanced flexibility. While analog circuitry is often tuned to the specific instrument 102 or family of instruments 102, digital signal processing can typically provide a great degree of flexibility through programmability of the digital signal processing element(s) to adapt to a wide variety of sensor types. Accordingly in some embodiments, digital signal processing provides the same or improved signal processing capabilities and greater flexibility compared to analog-intensive approaches, while offering a more compact implementation and reduced power consumption. In some such embodiments, these benefits can be realized in a smaller and less expensive PIM 112.

As shown in FIG. 2, the PIM 112 includes a signal separator 202, one or more analog-to-digital converters (e.g., ADCs 204 and 206), a signal processor 208, and an interface subunit 210. In the illustrated embodiment, the PIM 112 is configured to receive pressure and flow-related data from the instrument 102. It is understood that these data types are exemplary, and accordingly, components may be added to or subtracted from the PIM 112 based on the type of sensor data provided by the instrument 102.

Received sensor data may be first provided to the signal separator 202 of the PIM 112. In embodiments in which the instrument 102 supplies more than one type of data on the same set of electrical conductors or other communication pathway, the signal separator 202 discriminates between the data types to provide a different type or modality of data at each output. For example, in the illustrated embodiment, the signal separator 202 separates pressure data reported by the instrument 102 from flow-related data also reported by the instrument 102. In embodiments in which the instrument 102 supplies only a single type of data, the signal separator 202 may be omitted or disabled.

The mechanism by which the signal separator 202 operates depends in part on the manner in which the data is transmitted over the communications channel 110. In an embodiment, different types of data are reported on different conductors, and the signal separator 202 merely separates the conductors according to data type. In an embodiment, data is time-division multiplexed, and the signal separator 202 includes a time-division demultiplexer. In some embodiments, different data types have different characteristic frequencies, and the signal separator 202 includes a number of low-pass, high-pass, and/or band-pass filters. For example, in an embodiment, pressure data is reported as a DC and low-frequency signal (e.g., approximately 100 Hz and below), while the ultrasonic echo signal carrying the flow-related Doppler ultrasound echo signal has a higher characteristic frequency (e.g., in the ultrasonic frequency range, typically 10 MHz and higher). Accordingly, the signal separator 202 passes the composite signal through a low-pass filter to extract the pressure-related data and through a high-pass filter to extract the flow-related data. Of course, these embodiments are merely exemplary, and other types of signal separation are both contemplated and provided for.

After separation, one or more of the data signals may be amplified. In the illustrated embodiment, the flow data is amplified by the illustrated amplifier, while the pressure data is not. However, it is understood that in other embodiments, all, some, and/or none of the types of signal data are amplified prior to analog-to-digital conversion. The amplified or unamplified data is digitized using analog-to-digital converters such as ADCs 204 and 206. The ADCs 204 and 206 sample the analog signals at discrete times and provide the sample values in a digital format. The sampling rate used by the ADCs may be determined in part by the type of data being sampled and the characteristic frequencies thereof. For example, pressure data may vary relatively slowly, and so, in an embodiment, a sampling rate of approximately 200 Hz is provided to ADC 204. In some instances, the PIM 112 includes components for processing the pressure data as described in U.S. patent application Ser. No. 14/212,989, filed Mar. 14, 2014, now published as U.S. Patent Application Publication No. US 2014-0276143 A1 on Sep. 18, 2014, which is hereby incorporated by reference in its entirety.

In contrast to the low characteristic frequency of pressure data, flow velocity data produced by a Doppler ultrasound transducer may have a much higher characteristic frequency. Ultrasound transducers operate by emitting ultrasound waves centered on a nominal center frequency, and receiving the echo signals from surrounding tissues such as the vessel wall 104 and the moving blood within the vessel. Accordingly, in some embodiments, the relevant flow data (Doppler-shifted ultrasound echo signal) falls within a relatively narrow bandwidth centered around the nominal center frequency. Various exemplary ultrasound transducers used for intravascular Doppler flow measurement have nominal center frequencies between approximately 10 MHz and approximately 15 MHz. Other exemplary ultrasound transducers have nominal center frequencies of approximately 20 MHz or approximately 40 MHz. Due to its relatively high center frequency compared to its typically much narrower bandwidth, Doppler ultrasound echo signals are often converted to a baseband format prior to being digitized, in order to reduce the required ADC sampling rate. Baseband conversion mixes a narrow bandwidth, high-frequency signal with sine and cosine reference waveforms to produce a pair of low-frequency in-phase and quadrature signals, centered on zero frequency but covering the same bandwidth as the original echo signal. The resulting lower frequency signals can be faithfully represented by samples digitized at a much lower rate compared to that required to directly sample the original echo signal.

However, as will be discussed in further detail below, there are advantages to directly digitizing the Doppler-shifted ultrasound echo signal at a higher sampling rate, rather than using analog baseband conversion to reduce the sample rate requirement. In particular, analog baseband conversion introduces nonlinear signal distortion and mismatch between in-phase and quadrature channels, creating artifacts in the subsequent Doppler analysis, while direct digital sampling may utilize a single ADC to capture both in-phase and quadrature samples, thereby ensuring perfect matching to eliminate channel matching artifacts. In addition, analog baseband conversion circuitry requires careful tuning of the components to ensure optimum performance, and generally provides limited flexibility in adapting to different operating frequencies to support multiple device types. In contrast, direct digital sampling reduces or eliminates the need for tuning of the components, with any required calibration or tuning implemented in the digital domain through compensation coefficients stored in non-volatile memory. Furthermore the direct digital sampling approach offers a great deal of flexibility to accommodate different devices and signal processing algorithms by loading new firmware to control the sampling frequency and other signal processing parameters.

One particular variation of direct digital sampling is the digital quadrature sampling approach as described in greater detail below. According to this approach, in various embodiments, the flow ADC 206 digitizes the Doppler-shifted ultrasound echo signals at a sampling rate determined by the equation:

$$\text{Sampling Rate}=4/(2N+1)\times\text{Nominal Center Frequency}$$

where N is an integer greater than or equal to 0. In an exemplary embodiment, where the ultrasound transducer of the instrument 102 has a nominal center frequency of 12 MHz, N is selected to be 0 such that the flow data ADC 206 samples the Doppler-shifted ultrasound echo signal at 4 times the nominal center frequency (i.e., 48 MHz).

As an alternative to direct quadrature sampling, a high-speed ADC 206 may be used to sample the Doppler-shifted ultrasound echo signal at an arbitrary frequency greater than the Nyquist rate (i.e., greater than twice the highest frequency component in the echo signal). High-speed ADCs support very high sampling rates (in the GHz range and above). Thus, in some embodiments, ADC 206 is used to sample the flow data at a rate significantly greater than the Nyquist rate (e.g., 10 times the Nyquist rate or greater). In further exemplary embodiments, the flow data ADC 206 samples at pseudo-random intervals.

The digitized sensor data is provided to a signal processor 208, which may include an FPGA (field programmable gate array), an ASIC (application-specific integrated circuit), a programmable microcontroller, a microprocessor, and/or any other processing resource. In an embodiment, the signal processor 208 may perform baseband conversion, filtering, interpolation, noise reduction, integrate-and-hold, and/or other signal processing tasks on digitized Doppler-shifted ultrasound echo data before providing this processed, flow-related data to other components of the diagnostic system 100 such as the processing system 114 via the interface subunit 210.

Figure 3:
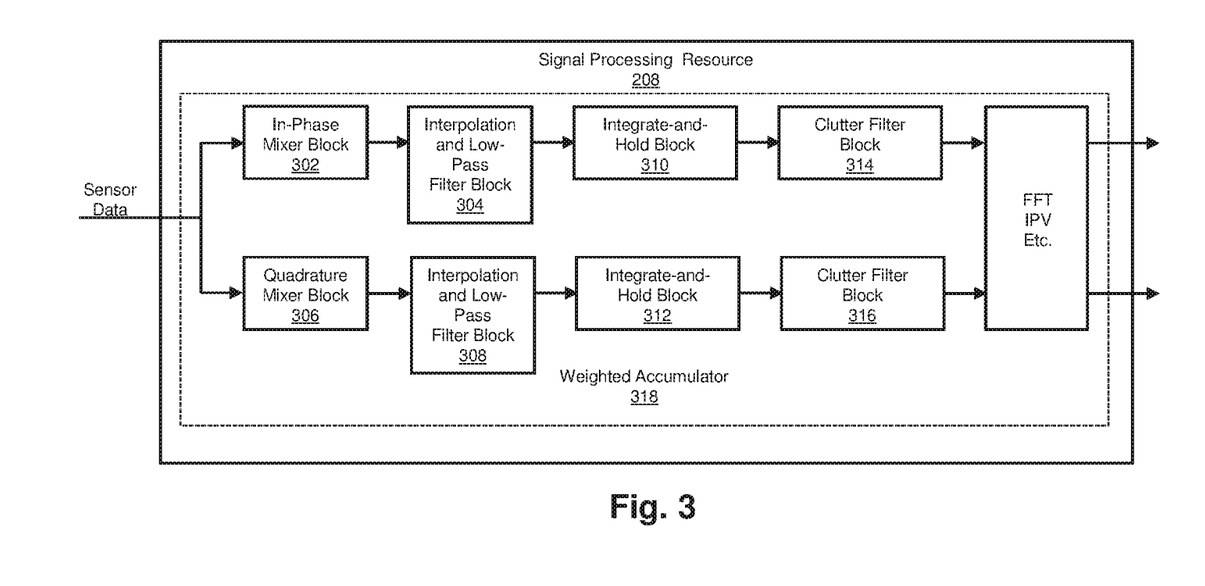
FIG. 3 is a diagrammatic schematic view of a signal processor of a PIM according to an embodiment of the present disclosure.

Referring now to FIG. 3, an exemplary signal processing resource 208 is illustrated in more detail. The illustrated logical blocks 302-316 represent hardware, firmware, software, and/or combinations thereof configured to perform various signal processing tasks on the sensor data. In the illustrated embodiment, the sensor data includes Doppler-shifted ultrasound echo signals representing blood flow data, and the signal processing blocks include mixer blocks 302 and 306 and low-pass filter blocks 304 and 308 that perform a baseband conversion of the digitized data. Similarly to baseband conversion in the analog domain, the digital baseband conversion blocks produce a set of low frequency baseband signals that represent the high frequency data. The underlying principle is that a time varying signal S(t) can be expressed as follows:

$$S(t)=I(t)\cos(2\pi f_c t)-Q(t)\sin(2\pi f_c t)$$

The two constituent signals, I(t) and Q(t), are referred to as the in-phase and quadrature components of S(t). This representation is useful because I(t) and Q(t) are frequency shifted downwards by $f_c$, referred to as the carrier frequency, and if the time varying signal has a narrow bandwidth around the carrier frequency, then the constituent signals are similarly narrow in bandwidth around zero frequency. In this case, the time varying signal is fully represented by the two constituent signals combined with knowledge of the chosen carrier frequency, while in many cases the low frequency constituent signals I(t) and Q(t) are easier to manipulate than their high-frequency counterpart S(t) in the subsequent signal processing steps. In many embodiments, $f_c$ is selected to be equal to the nominal center frequency of the ultrasound transducer used to obtain the Doppler flow data. To obtain I(t), the digitized sensor data is mixed (multiplied) with a cosine reference waveform $\cos(2\pi f_c t)$ in the in-phase mixer block 302 and then low-pass filtered by filter block 304 to remove the unwanted high frequency component. To obtain Q(t), the digitized sensor data is mixed with a sine reference waveform $\sin(2\pi f_c t)$ in the quadrature mixer block 306 and low-pass filtered by filter block 308 to remove the unwanted high frequency component.

The in-phase mixer block 302 of the signal processor 208 may be implemented with a multiplier supplied with samples of the reference waveform $\cos(2\pi f_c t)$ as coefficients, and the quadrature mixer block 306 may be implemented with a multiplier supplied with samples of the reference waveform $\sin(2\pi f_c t)$ as coefficients. In embodiments in which the sampling rate conforms to the equation:

Sampling Rate=$4/(2N+1)$×Nominal Center Frequency these coefficients are trivial. For example, when N=0 and $f_c$ is selected to be the nominal center frequency of the ultrasound transducer, the digitized samples of the reference waveform $\cos(2\pi f_c t)$ are [1,0,−1,0,1,0,−1,0, . . . ] and the digitized samples of the reference waveform $\sin(2\pi f_c t)$ are [0,1,0,−1,0,1,0,−1, . . . ]. With these simple coefficients, the normally complex digital multiplication blocks generally needed for quadrature mixing can be reduced to simple digital logic. Furthermore, the ADC samples that contribute to the in-phase component are the odd samples only, while the samples that contribute to the quadrature component are the even samples only. This separation between in-phase and quadrature components, facilitated by digital quadrature sampling, simplifies the subsequent signal processing operations by cutting in half the number of samples that contribute to the various intermediate results (such as the low-pass filter or the integrate-and-hold outputs).

In alternative embodiments using high frequency analog-to-digital conversion at an arbitrary rate (as opposed to direct digital quadrature sampling), the reference waveform coefficients are not so simple and furthermore each sample may contribute to both the in-phase and quadrature components. With these nontrivial coefficients, a pair of high-speed digital multipliers is needed to implement the mixer blocks 302 and 306, and each of these mixer blocks would need to process both even and odd samples. But even with this added complexity, the required high-speed multipliers can easily be incorporated into an FPGA-based (or other) implementation.

As further illustrated in FIG. 3, the in-phase and quadrature outputs from the mixer blocks 302 and 306 are subsequently processed by interpolation and low-pass filter blocks 304 and 308. Interpolation provides in-phase and quadrature samples that correspond to the same instant in time, and it is particularly advantageous with respect to direct quadrature sampling, since that sampling process naturally provides in-phase and quadrature samples that are offset from each other by a time shift equal to the sampling period of the direct quadrature sampling. In general, interpolation is implemented by a band-pass filter, however in the case of baseband signals centered on zero frequency, interpolation is implemented with a simple low-pass filter. It is convenient to implement interpolation with a finite impulse response (FIR) filter, in which case the interpolation filter coefficients can be combined (by convolution) with the low-pass filter coefficients such that both operations can be performed together in a single step.

Once the in-phase and quadrature components, I(t) and Q(t), are determined, the signal processor 208 may perform other signal processing tasks. In an embodiment, the signal processor 208 performs an integrate-and-hold process to implement range selectivity, define a range gate depth, limit the bandwidth, and improve the signal-to-noise ratio. The in-phase and quadrature outputs from the interpolation and low-pass filter blocks 304 and 308 are processed by integrate-and-hold blocks 310 and 312 to produce the range-gated baseband Doppler signals. The integrate-and-hold step is performed in the digital domain by simply accumulating (summing) the chosen number of successive samples (corresponding to the range gate width) after the desired delay from the initial transmit pulse (corresponding to the range gate depth). The integration operation produces a low-pass filtering effect with a cutoff frequency nominally equal to the inverse of the integration time, while the signal-to-noise ratio is improved by averaging as the square root of the number of samples accumulated by the integrator.

Each of the three types of signal processing blocks described in the foregoing paragraphs (mixer, interpolation/filter, and integrate-and-hold) produces an output which is a linear combination of the input samples to that block. By the principles of linearity, a linear combination of linear combinations is itself a linear combination of the original inputs, and accordingly, all three of these processing steps can be combined into a single mathematical operation which simply provides a weighted sum (i.e., a linear combination) of the input samples from the ADC. In this case, the weighting coefficients for the composite operation incorporate the coefficients needed for baseband mixing, interpolation, low-pass filtering, and integration, and a single multiplier/accumulator element can provide the mixer, interpolation/low-pass filter, and integrate-and-hold functions in blocks 302, 304, and 310 for the in-phase channel, or in blocks 306, 308, and 312 for the quadrature channel.

In an embodiment, the signal processor 208 performs clutter filtering in blocks 314 and 316 to remove the ultrasound echo contributions due to stationary and slow moving tissues. In some embodiments, clutter filtering follows baseband conversion in the mixer and low-pass filter blocks, and range gate selection in the integrate-and-hold block to remove the stationary and low frequency components present in the range-gated baseband Doppler signals. Clutter filtering can be implemented after FFT (Fast Fourier Transform) processing transforms the Doppler signals to the frequency domain, by simply blanking the low frequency bins of the spectrum. Alternatively, clutter filtering can be performed in a time domain operation prior to the FFT. The time domain clutter filter prior to FFT is advantageous in terms of reducing the dynamic range within the FFT computations required to preserve the low level flow blood flow components of the Doppler spectrum in the presence of large, low-frequency clutter components. The time domain clutter filter can be implemented with a relatively simple algorithm consisting of a boxcar average (accumulator) and subtraction, or it can use a more elaborate high-pass filter implemented with an IIR (infinite impulse response) or FIR (finite impulse response) architecture.

In various embodiments, the signal processor 208 performs additional signal processing such as fast Fourier transform (FFT) on the in-phase and quadrature components and/or instantaneous peak velocity (IPV) processing on the spectral output from the FFT. Subsequently, the signal processor 208 provides the processed in-phase and quadrature components to the interface subunit 210 for delivery to other components of the diagnostic system 100 such as the processing system 114.

Figure 4:
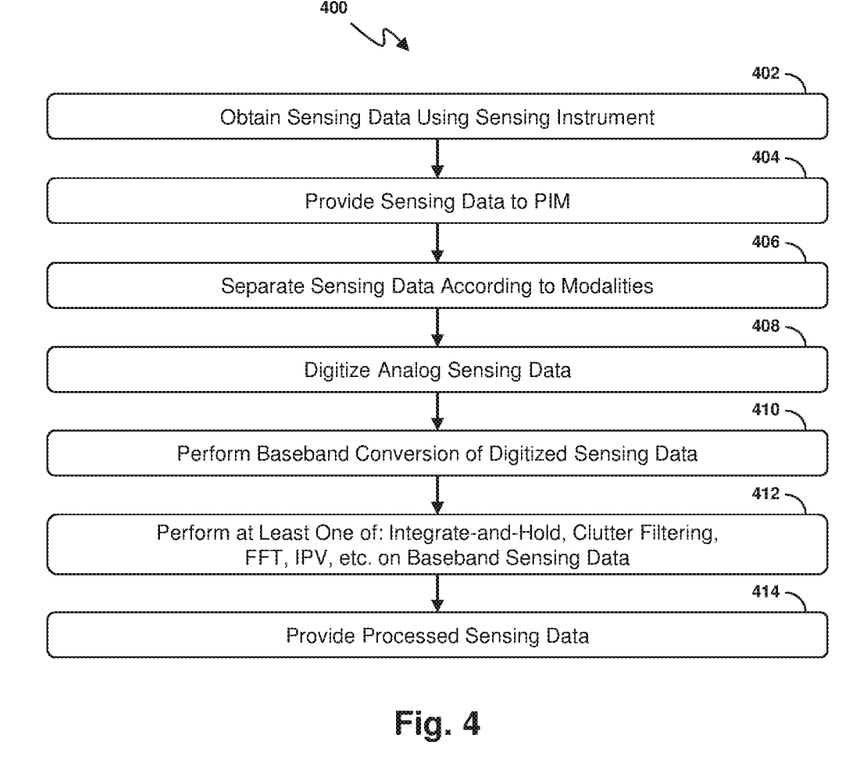
FIG. 4 is a flow diagram illustrating steps for receiving and processing medical sensor data by the diagnostic system according to an embodiment of the present disclosure.

Referring now to FIG. 4, a method 400 of processing sensor data using the diagnostic system 100 of FIGS. 1-3 is illustrated according to an embodiment of the present disclosure. It is understood that additional steps can be provided before, during, and after the steps of method 400, and that some of the steps described can be replaced or eliminated for other embodiments of the method.

Referring to block 402, medical sensor data is obtained. In some embodiments, an intravascular device such as the aforementioned instrument 102 is advanced into a vessel 104. Sensors 106 disposed on the instrument 102 are activated and used to obtain the medical sensor data. Accordingly, the medical sensor data includes one or more data modalities such as flow (velocity), flow (volume), pressure, images, temperature, and/or combinations thereof. In one such embodiment, the medical sensor data includes both Doppler ultrasound blood flow sensor data and pressure sensor data. The obtained medical sensor data is provided to a PIM 112 via a communications channel 110 as shown in block 404.

Referring to block 406, in an embodiment, a signal separator 202 within the PIM 112 separates the medical sensor data according to the respective modalities. For example, the signal separator 202 may separate Doppler ultrasound blood flow sensor data from pressure sensor data according to their different characteristic frequencies.

Referring to block 408, one or more ADCs of the PIM 112 digitize the medical sensor data thereby converting it from an analog format to a digital format. The ADCs sample the analog signal at discrete times and provide the sampled values in a digital format. In an exemplary embodiment of Doppler ultrasound based blood flow sensor data, it may be advantageous to perform digital quadrature sampling at an ADC sampling rate specified by the equation:

Sampling Rate=4/(2N+1)×Nominal Center Frequency where N is an integer greater than or equal to 0. In some embodiments, N is selected to be 0 to provide a sampling rate 4 times the nominal center frequency. This sampling rate provides digital quadrature sampling to simplify the subsequent signal processing, and it is far higher than the Nyquist rate minimally required to faithfully capture the full bandwidth of the signal. The over-sampled data can provide increased signal-to-noise ratio with respect to ADC quantization noise through sample averaging. In other embodiments, an ADC samples the Doppler ultrasound based blood flow sensor data at a rate significantly greater than the Nyquist rate (e.g., 10 times the Nyquist rate) and/or at a pseudo-random sampling intervals.

Referring to block 410, a signal processor 208 of the PIM 112 performs a baseband conversion on the digitized sensor data. The baseband conversion produces a set of low frequency signals that represent the high frequency, narrow bandwidth sensor data. The digitized sensor data is mixed (multiplied) with a cosine reference waveform $\cos(2\pi f_c t)$ and low-pass filtered to obtain an in-phase component. The digitized sensor data is mixed (multiplied) with a sine reference waveform $\sin(2\pi f_c t)$ and low-pass filtered to obtain a quadrature component. In various embodiments, the baseband conversion is performed by a single weighted accumulator, while in other embodiments the baseband conversion is performed by a pair of weighted accumulators, one for the in-phase component and the other for the quadrature component.

Referring to block 412, the signal processor 208 of the PIM 112 performs additional processing on the baseband converted sensor data. This may include an integrate-and-hold process, clutter filtering, FFT, WV, and/or other suitable processing steps. Referring to block 414, the processed sensor data is provided to other components of the diagnostic system 100 such as the processing system 114 via an interface subunit 210 of the PIM. The processed sensor data may then be used for any suitable purpose including diagnostic assessment of the vessel 104. In various embodiments, the integrate-and-hold process is performed using the same weighted accumulator(s) used to perform the baseband conversion by mixing and filtering.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A medical diagnostic system comprising:
   an intravascular guidewire configured to be positioned within a blood vessel of a patient, wherein the intravascular guidewire comprises a distal portion with an intravascular blood flow sensor configured to generate intravascular blood flow data and an intravascular pressure sensor configured to generate intravascular pressure data, wherein the intravascular blood flow data and the intravascular pressure data are time-division multiplexed; and
   a patient interface module (PIM) configured for communication with a processing system and the intravascular guidewire,
   wherein the patient interface module is distinct from the intravascular guidewire and the processing system,
   wherein the patient interface module is communicatively interposed between the intravascular guidewire and the processing system,
   wherein the patient interface module includes:
      a signal separator configured to receive the time-division multiplexed intravascular blood flow data and intravascular pressure data directly from the intravascular guidewire, wherein the signal separator comprises a time-division de-multiplexer operable to separate the intravascular blood flow data and the intravascular pressure data;
      an analog-to-digital converter operable to:
         receive the intravascular blood flow data from the time-division de-multiplexer; and
         perform an analog-to-digital conversion on the intravascular blood flow data to produce digital intravascular blood flow data, wherein the analog-to-digital conversion is performed in the PIM and not the intravascular guidewire or the processing system; and
      an interface subunit operable to output the digital intravascular blood flow data to the processing system.

2. The medical diagnostic system of claim 1, wherein the intravascular blood flow sensor is operable to provide the intravascular blood flow data to the patient interface module.

3. The medical diagnostic system of claim 1,
wherein the analog-to-digital converter is further operable to:
receive the intravascular pressure data from the time-division de-multiplexer; and
perform the analog-to-digital conversion on the intravascular pressure data.

4. The medical diagnostic system of claim 3, wherein the interface subunit is operable to output digital intravascular pressure data to the processing system.

5. The medical diagnostic system of claim 1, further comprising:
a signal processing resource operable to perform a baseband conversion on the digital intravascular blood flow data to produce baseband intravascular blood flow data.

6. The medical diagnostic system of claim 5, wherein the signal processing resource includes a weighted accumulator operable to perform the baseband conversion on the digital intravascular blood flow data.

7. The medical diagnostic system of claim 6, wherein the weighted accumulator is further operable to perform:
in-phase signal mixing on the digital intravascular blood flow data to produce an in-phase component;
quadrature signal mixing on the digital intravascular blood flow data to produce a quadrature component; and
interpolation and low-pass filtering on the in-phase component and the quadrature component.

8. The medical diagnostic system of claim 6, wherein the weighted accumulator includes an in-phase weighted accumulator and a quadrature accumulator.

9. The medical diagnostic system of claim 6,
wherein the intravascular blood flow sensor comprises an ultrasound transducer,
wherein the intravascular blood flow data is obtained using a nominal center frequency of the ultrasound transducer, and
wherein the weighted accumulator includes first and second sets of coefficients selected to:
mix the digital intravascular blood flow data with a signal $\cos(2\pi f_c t)$, where $f_c$ is equal to the nominal center frequency in order to obtain an in-phase component;
mix the digital intravascular blood flow data with a signal $\sin(2\pi f_c t)$, where $f_c$ is equal to the nominal center frequency in order to obtain a quadrature component; and
low-pass filter the in-phase component and the quadrature component.

10. The medical diagnostic system of claim 9, wherein the first and second sets of coefficients are further selected to perform at least one of: a sample-and-hold process or clutter filtering.

11. The medical diagnostic system of claim 6, further comprising the processing system, wherein the processing system is operable to obtain a measurement of blood flow based on the baseband intravascular blood flow data and to display the measurement of blood flow on a user display.

12. The medical diagnostic system of claim 1, wherein the analog-to-digital conversion is performed before a baseband conversion on the digital intravascular blood flow data is performed.

13. The medical diagnostic system of claim 12, wherein, to perform the analog-to-digital conversion, the analog-to-digital converter is configured to sample the intravascular blood flow data according to a sampling rate based on a characteristic frequency of the intravascular blood flow data.

14. The medical diagnostic system of claim 13,
wherein the intravascular blood flow sensor comprises an ultrasound transducer,
wherein the sampling rate is equal to four times a nominal center frequency of the ultrasound transducer used to obtain the intravascular blood flow data.

15. The medical diagnostic system of claim 13, wherein the sampling rate is defined by an equation:

sampling rate=$4/(2N+1)\times$a nominal center frequency where N is an integer greater than or equal to zero.

16. The medical diagnostic system of claim 15,
wherein the intravascular blood flow sensor comprises an ultrasound transducer,
wherein a carrier frequency is chosen to be equal to the nominal center frequency of the ultrasound transducer.

17. The medical diagnostic system of claim 15, wherein a value of N corresponds to the sampling rate being at least a Nyquist rate of the intravascular blood flow data.

18. The medical diagnostic system of claim 1, wherein the intravascular blood flow data comprises velocity data.

* * * * *